(12) United States Patent
Yoo et al.

(10) Patent No.: US 11,450,410 B2
(45) Date of Patent: Sep. 20, 2022

(54) APPARATUS AND METHOD FOR GENERATING MOLECULAR STRUCTURE

(71) Applicant: SAMSUNG ELECTRONICS CO., LTD., Suwon-si (KR)

(72) Inventors: Jiho Yoo, Hwaseong-si (KR); Youngmin Nam, Seoul (KR); Dongseon Lee, Suwon-si (KR); Younsuk Choi, Seongnam-si (KR); Youngchun Kwon, Yongin-si (KR); Kyungdoc Kim, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 510 days.

(21) Appl. No.: 16/402,410

(22) Filed: May 3, 2019

(65) Prior Publication Data

US 2019/0355444 A1   Nov. 21, 2019

Related U.S. Application Data

(60) Provisional application No. 62/673,377, filed on Jul. 18, 2018.

(30) Foreign Application Priority Data

Jul. 18, 2018   (KR) .......................... 10-2018-0083650

(51) Int. Cl.
    *G01N 33/48* (2006.01)
    *G01N 33/50* (2006.01)
    (Continued)

(52) U.S. Cl.
    CPC ............. *G16C 20/50* (2019.02); *G06F 30/00* (2020.01); *G06N 3/08* (2013.01); *G16C 20/70* (2019.02); *G16C 20/80* (2019.02)

(58) Field of Classification Search
    CPC ........ G16C 20/50; G16C 20/70; G16C 20/80; G06F 30/00; G06N 3/08
    See application file for complete search history.

(56) References Cited

U.S. PATENT DOCUMENTS

2001/0056329 A1   12/2001   Smellie et al.
2008/0235167 A1    9/2008   Beratan et al.
(Continued)

FOREIGN PATENT DOCUMENTS

JP   2002-506447 A      2/2002
WO   WO-9428504 A1 * 12/1994 ............. G16C 20/50
WO   2006/023574 A2    3/2006

OTHER PUBLICATIONS

Goldfuss et al. Aromaticity in Group 14 metalloles: Structural, energetic, and magnetic criteria. Organometallics, vol. 16, pp. 1543-1552. (Year: 1997).*

(Continued)

*Primary Examiner* — Russell S Negin
(74) *Attorney, Agent, or Firm* — Sughrue Mion, PLLC

(57) ABSTRACT

A method of generating a molecular structure includes generating, based on a predetermined number of a plurality of nodes, all possible two-dimensional (2D) graphs and a plurality of edges representing connections between the plurality of nodes and, for each 2D graph from among the generated 2D graphs, generating all possible molecular structures based on the 2D graph by substituting each of the plurality of nodes with a polygonal ring structure including carbon atoms and substituting the edges with bonds between polygonal ring structures. Also, a method includes substituting at least one of carbon atoms included in the polygonal ring structures with an atom other than a carbon atom.

17 Claims, 13 Drawing Sheets

(51) Int. Cl.
    *G16C 20/50*     (2019.01)
    *G16C 20/70*     (2019.01)
    *G06N 3/08*     (2006.01)
    *G16C 20/80*     (2019.01)
    *G06F 30/00*     (2020.01)

(56) References Cited

U.S. PATENT DOCUMENTS

| 2010/0205214 | A1 | 8/2010 | Fliri et al. |
| 2011/0264432 | A1 | 10/2011 | Penner et al. |
| 2015/0269356 | A1 | 9/2015 | Pallai et al. |

OTHER PUBLICATIONS

Cioslowski et al., "Is Superbenzene Superaromatic?", J. Am. Chem. Soc., vol. 113, 1991, pp. 1086-1089, 4 pages total.

Tošić et al., "Enumeration of Polyhex Hydrocarbons to h=17", J. Chem. Inf. Comput. Sci., vol. 35, 1995, pp. 181-187, 7 pages total.

Dias, "The polyhex/polypent topological paradigm: regularities in the isomer numbers and topological properties of select subclasses of benzenoid hydrocarbons and related systems", Chemical Society Reviews, vol. 39, 2010, pp. 1913-1924, 12 pages total.

Dias, "A Periodic Table for Polycyclic Aromatic Hydrocarbons. Isomer Enumeration of Fused Polycyclic Aromatic Hydrocarbons", Journal of Chemical Information and Computer Science, vol. 22, 1982, pp. 15-22, 8 total pages.

Slanina, "Chemical Graphs Enumeration and Chemical Reactivity: Thermodynamic and Kinetic Considerations", Discrete Applied Mathematics, vol. 19, 1988, pp. 349-365, 17 pages total.

Mata, et al., "Sprout: 3D Structure Generation Using Templates", 1995, J. Chem. Inf. Comput. Sci. vol. 35, 15 pages total.

Li, et al., "Ion implantation of low energy Si into graphene: insight from computational studies", 2015, RSC Advances, vol. 5, 7 pages total.

Kier, et al., "Design of Molecules from Quantitative Structure-Activity Relationship Models", 1993, J. Chem. Inf. Comput. Sci. vol. 33, 5 pages total.

Montavon, et al., "Machine learning of molecular electronic properties in chemical compound space", 2013, New Journal of Physics, vol. 15, 17 pages total.

Communication issued Jun. 14, 2022 by the Korean Intellectual Property Office for Korean Patent Application No. 10-2018-0083650.

* cited by examiner

- HEXAGONAL-HEXAGONAL-HEXAGONAL

- HEXAGONAL-HEXAGONAL-PENTAGONAL

- HEXAGONAL-PENTAGONAL-HEXAGONAL

- HEXAGONAL-PENTAGONAL-PENTAGONAL

- PENTAGONAL-HEXAGONAL-PENTAGONAL

- PENTAGONAL-PENTAGONAL-PENTAGONAL 3-2. △            4-1. ↑            5-11. ⩕
· 6-6-6     · 6-6-6-6

(262)

(332)

APPARATUS AND METHOD FOR GENERATING MOLECULAR STRUCTURE

CROSS-REFERENCE TO RELATED APPLICATIONS

This application is based on and claims priority under 35 U.S.C. § 120 to U.S. Patent Application No. 62/673,377, filed on May 18, 2018, in the U.S. Patent and Trademark Office, and under 35 U.S.C. § 119 to Korean Patent Application No. 10-2018-0083650, filed on Jul. 18, 2018, in the Korean Intellectual Property Office, the disclosures of which are incorporated by reference herein in their entireties.

BACKGROUND

1. Field

The present disclosure relates to apparatuses and methods for generating a molecular structure.

2. Description of the Related Art

With the recent development of computerized screening methods for the development of new materials, it has become possible to quickly evaluate a large number of new material candidates. The evaluation of new material candidates has been performed by using methods of searching for a specific material group or arbitrarily transforming materials based on an algorithm. For example, new material candidates have been evaluated by generating a virtual candidate material group and evaluating the generated virtual candidate material group by using a method of determining a specific partial structure and then randomly modifying an existing structure by applying a genetic algorithm.

However, because the modification is random, there is a lack of systematic new material generation methodology for the entire candidate material group, and a structure may be omitted during a search for new materials. Accordingly, there is a need for a method of generating an available candidate material without omitting any possible materials to perform an effective search.

SUMMARY

Provided are apparatuses and methods for generating a molecular structure.

Additional aspects will be set forth in part in the description which follows and, in part, will be apparent from the description, or may be learned by practice of the presented embodiments.

In accordance with an aspect of the disclosure, a method of generating a molecular structure includes generating two-dimensional (2D) graphs of all possible combinations including a plurality of nodes and edges representing connections between the plurality of nodes based on a number of the plurality of nodes constituting a 2D graph; converting the 2D graphs into first molecular structures of all possible combinations by substituting each of the plurality of nodes with a polygonal ring structure including carbon atoms and substituting the edges with bonds between polygonal ring structures; and generating final molecular structures of all possible combinations by substituting at least one of the carbon atoms included in the first molecular structures with an atom other than the carbon atoms.

The generating of the final molecular structures may include generating second molecular structures of all possible combinations by substituting any one of the carbon atoms in the first molecular structures with a metal atom; and generating the final molecular structures of all possible combinations by substituting at least one of carbon atoms included in the second molecular structures with any one of nitrogen (N), oxygen (O), phosphorus (P), sulfur (S), selenium (Se), and silicon (Si).

The polygonal ring structure may be any one of a pentagonal ring structure and a hexagonal ring structure.

Each of the 2D graphs may include three to five nodes.

The converting of the 2D graphs into the first molecular structures may include selecting a 2D graph corresponding to a molecular structure corresponding to a predetermined condition from the 2D graphs; and converting the selected 2D graph into the first molecular structures of all possible combinations by substituting each of the plurality of nodes constituting the selected 2D graph with the polygonal ring structure including the carbon atoms and substituting the edges with the bonds between polygonal ring structures.

The generating of the second molecular structures may include generating the second molecular structures of all possible combination by substituting a carbon atom having a bond order of 2 among the carbon atoms included in the first molecular structures with the metal atom.

The generating of the final molecular structures may include selecting a second molecular structure in which a bond order of adjacent carbon atoms adjacent to the metal atom is 3 from the second molecular structures; and generating the final molecular structures of all possible combinations by substituting at least one of carbon atoms included in the selected second molecular structure with any one of nitrogen (N), oxygen (O), phosphorus (P), sulfur (S), selenium (Se), and silicon (Si).

An adjacent ring structure adjacent to a ring structure including the metal atom may be an aromatic ring.

The method may further include selecting some of the final molecular structures; calculating a specific property value with respect to each of the selected final molecular structures; and training a neural network by using a descriptor of the selected final molecular structures as input data of the neural network and using the specific property value corresponding to each of the selected final molecular structures as output data of the neural network.

The method may further include calculating a specific property value with respect to an arbitrary molecular structure by using at least some of the generated final molecular structures and a neural network trained based on matching data obtained by matching a specific property value with respect to each of the at least some final molecular structures.

In accordance with an aspect of the disclosure, an apparatus for generating a molecular structure includes a memory storing at least one program; and a processor configured to drive the apparatus for generating the molecular structure by executing the at least one program, wherein the processor is further configured to generate two-dimensional (2D) graphs of all possible combinations including a plurality of nodes and edges representing connections between the plurality of nodes based on a number of the plurality of nodes constituting a 2D graph, convert the 2D graphs into first molecular structures of all possible combinations by substituting each of the plurality of nodes with a polygonal ring structure including carbon atoms and substituting the edges with bonds between polygonal ring structures, and generate final molecular structures of all possible combinations by substituting at least one of the carbon atoms included in the first molecular structures with an atom other than the carbon atoms.

In accordance with an aspect of the disclosure, a computer-readable recording medium includes a program, which when executed by a computer, performs the method.

In accordance with an aspect of the disclosure, a method of generating a molecular structure includes generating, based on a predetermined number of a plurality of nodes, all possible two-dimensional (2D) graphs including the predetermined number of nodes and a plurality of edges representing connections between the plurality of nodes; for each 2D graph from among the generated 2D graphs, generating all possible molecular structures based on the 2D graph by substituting each of the plurality of nodes with a polygonal ring structure including carbon atoms, substituting the plurality of edges with bonds between polygonal ring structures; and substituting at least one of the carbon atoms included in the polygonal ring structures with an atom other than a carbon atom.

The substituting the at least one of the carbon atoms may include substituting a first carbon atom from among the carbon atoms included in the polygonal ring structures with a metal atom; and substituting at least one second carbon atom from among the carbon atoms included in the polygonal ring structures with any one of nitrogen (N), oxygen (O), phosphorus (P), sulfur (S), selenium (Se), and silicon (Si).

Each of the polygonal ring structures may be any one from among a pentagonal ring structure and a hexagonal ring structure.

Each of the generated 2D graphs may include three to five nodes.

The generating the molecular structures may include selecting a 2D graph that corresponds to a molecular structure having a predetermined condition from among the generated 2D graphs; and converting the selected 2D graph into the all possible molecular structures by substituting each of the plurality of nodes constituting the selected 2D graph with the polygonal ring structure including the carbon atoms and substituting the edges with the bonds between polygonal ring structures.

The first carbon atom may be a carbon atom having a bond order of 2 from among the carbon atoms included in the polygonal ring structures.

A bond order of adjacent carbon atoms adjacent to the metal atom may be 3.

An adjacent polygonal ring structure adjacent to a polygonal ring structure including the metal atom may be an aromatic ring.

The method may further include selecting some of the generated molecular structures; calculating a specific property value with respect to each of the selected molecular structures; and training a neural network by using a descriptor of the selected molecular structures as input data of the neural network and using the specific property value corresponding to each of the selected molecular structures as output data of the neural network.

The method may further include calculating a specific property value with respect to an arbitrary molecular structure from among the generated molecular structures by using at least some of the generated molecular structures and a neural network, the neural network being trained based on matching data obtained by matching each of the at least some of the generated molecular structures with a corresponding property value.

In accordance with an aspect of the disclosure, an apparatus for generating a molecular structure includes a memory storing at least one program; and a processor configured to drive the apparatus for generating the molecular structure by executing the at least one program, wherein the processor is further configured to generate, based on a predetermined number of a plurality of nodes, all possible two-dimensional (2D) graphs including the predetermined number of nodes and a plurality of edges representing connections between the plurality of nodes, for each 2D graph from among the generated 2D graphs, generating all possible molecular structures based on the 2D graph by substituting each of the plurality of nodes with a polygonal ring structure comprising carbon atoms, substituting the plurality of edges with bonds between polygonal ring structures, and substituting at least one of the carbon atoms included in the polygonal ring structures with an atom other than a carbon atom.

The processor may be further configured to substitute a first carbon atom from among the carbon atoms included in the first molecular structures with a metal atom and substitute at least one second carbon atom from among the carbon atoms included in the polygonal ring structures with any one of nitrogen (N), oxygen (O), phosphorus (P), sulfur (S), selenium (Se), and silicon (Si).

Each of the polygonal ring structures may be any one from among a pentagonal ring structure and a hexagonal ring structure.

Each of the generated 2D graphs may include three to five nodes.

The processor may be further configured to select a 2D graph that corresponds to a molecular structure having a predetermined condition from among the generated 2D graphs and convert the selected 2D graph into the all possible molecular structures by substituting each of the plurality of nodes constituting the selected 2D graph with the polygonal ring structure comprising the carbon atoms and substituting the edges with the bonds between polygonal ring structures.

The first carbon atom may be a carbon atom having a bond order of 2 from among the carbon atoms included in the polygonal ring structures.

A bond order of adjacent carbon atoms adjacent to the metal atom may be 3.

An adjacent polygonal ring structure adjacent to a polygonal ring structure comprising the metal atom may be an aromatic ring.

The processor may be further configured to calculate a specific property value with respect to an arbitrary molecular structure from among the generated molecular structures by using at least some of the generated molecular structures and a neural network, the neural network being trained based on matching data obtained by matching each of the at least some of the generated molecular structures with a corresponding property value.

In accordance with an aspect of the disclosure, a non-transitory computer readable recording medium includes a program, which when executed by a computer, performs a method of generating a molecular structure including generating, based on a predetermined number of a plurality of nodes, all possible two-dimensional (2D) graphs including the predetermined number of nodes and a plurality of edges representing connections between the plurality of nodes; for each 2D graph from among the generated 2D graphs, generating all possible molecular structures based on the 2D graph by substituting each of the plurality of nodes with a polygonal ring structure including carbon atoms, substituting the plurality of edges with bonds between polygonal ring structures; and substituting at least one of the carbon atoms included in the polygonal ring structures with an atom other than a carbon atom.

BRIEF DESCRIPTION OF THE DRAWINGS

The above and other aspects, features, and advantages of certain embodiments of the present disclosure will be more apparent from the following description taken in conjunction with the accompanying drawings, in which.

DETAILED DESCRIPTION

Figure 1:
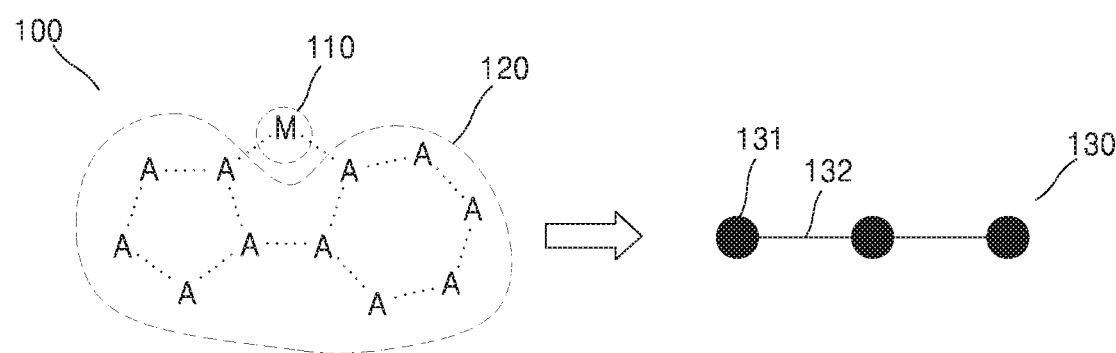
FIG. 1 is a diagram for explaining an example of a two-dimensional (2D) graph including nodes and edges according to an embodiment.
Figure 1:
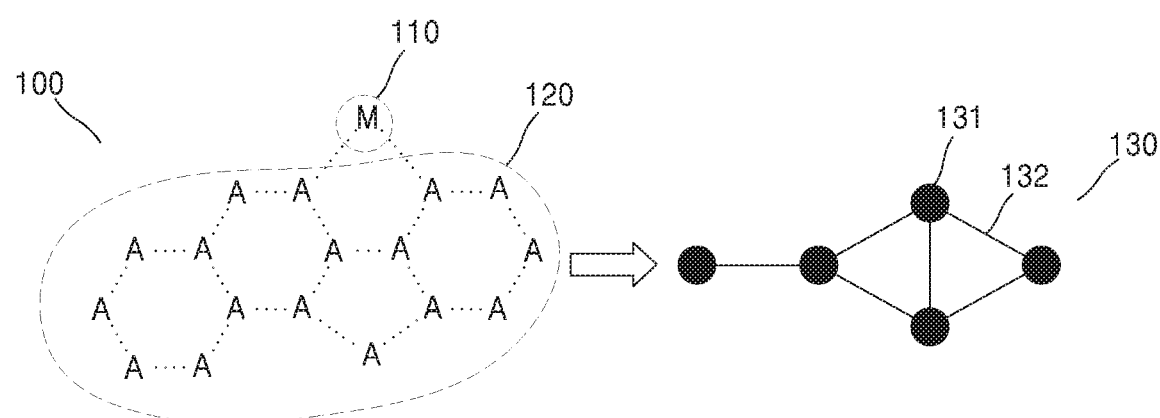

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of" and "at least one from among", when preceding a list of elements, modify the entire list of elements and do not modify the individual elements of the list.

The terms "according to some embodiments" or "according to an embodiment" used throughout the specification do not necessarily indicate the same embodiment.

Some embodiments of the present disclosure may be represented by functional block configurations and various processing operations. Some or all of these functional blocks may be implemented using various numbers of hardware and/or software components that perform particular functions. For example, the functional blocks of the present disclosure may be implemented using one or more microprocessors or circuits for a given function. Also, for example, the functional blocks of the present disclosure may be implemented in various programming or scripting languages. The functional blocks may be implemented with algorithms running on one or more processors. The present disclosure may also employ conventional techniques for electronic configuration, signal processing, and/or data processing. The terms "mechanism", "element", "unit" and "configuration" may be used in a broad sense and are not limited to mechanical and physical configurations.

Also, connection lines or connection members between the components illustrated in the drawings are merely illustrative of functional connections and/or physical or circuit connections. In actual devices, connections between the components may be represented by various functional connections, physical connections, or circuit connections that may be replaced or added.

With respect to the terms used herein, a descriptor that is data used in a neural network system refers to an indicator value used to describe characteristics of a substance and may be acquired by performing a relatively simple computation on a given substance. According to an embodiment, a descriptor may include a molecular structure fingerprint indicating whether or not a particular partial structure is included (e.g., Morgan fingerprint and extended connectivity fingerprint (ECFP)). The descriptor may include a quantitative structure-property relationship (QSPR) configured with a value that may immediately be calculated such as a molecular weight or the number of a partial structure (e.g., ring) included in a molecular structure.

Also, a structure refers to an atomic level structure of a substance. In order to derive a property by performing First Principles Calculation, the structure is required to be expressed at an atomic level. Thus, a structure of a substance needs to be derived to an atomic level to generate a novel chemical structure. The structure may be a structural formula based on atomic bonding relationships or a character string in a simple format (one-dimensional). The format of the character string expressing the structure may be a Simplified Molecular-input Line-entry System (SMILES) code, a Smiles Arbitrary Target Specification (SMARTS) code, an International Chemical Identifier (InChi) code, or the like.

Hereinafter, embodiments of the present disclosure will be described in detail with reference to the accompanying drawings.

FIG. 1 is a diagram for explaining an example of a two-dimensional (2D) graph 130 including nodes 131 and edges 132 according to an embodiment.

Any molecular structure may be represented as a 2D graph including nodes and edges. In general, each atom included in a molecular structure may be represented as a node of the 2D graph, and a bond between atoms may be represented as an edge representing a connection between nodes. However, when each atom is represented as the node of the 2D graph, the number of possible 2D graphs for a given number of nodes increases rapidly since the number of atoms increases. Accordingly, a method of representing each atom as the node of the 2D graph may not be suitable for expressing the molecular structure including several tens of atoms.

Hereinafter, a method of representing a molecular structure including a large number of atoms with a smaller number of nodes will be described. In this method, instead of mapping atoms to nodes in a 2D graph, a ring structure of a polygon corresponds to a node.

Referring to FIG. 1, a metal complex compound 100 includes a metal atom 110 and a ligand 120. The metal complex compound 100 may be formed through coordination bonding of isolated electron pairs of the ligand 120 to the central metal atom 110 having many empty orbitals.

In an embodiment, the metal complex compound 100 may include a plurality of ring structures. The ring structure constituting the metal complex compound 100 may be either a pentagonal ring structure or a hexagonal ring structure. Also, at least some of the plurality of ring structures constituting the metal complex compound 100 may be aromatic rings. The metal atom 110 may be a platinum group element. In an embodiment, the metal atom 110 may include iridium (Ir), platinum (Pt), gold (Au), or osmium (Os). However, the ring structure and the metal atom 110 are not limited to the above-mentioned examples.

The metal complex compound 100 may be represented by the 2D graph 130 including the nodes 131 and the edges 132. At this time, each ring structure of the metal complex compound 100 may be represented by nodes 131 of the 2D graph 130, and an atomic bond between ring structures may be represented by edges 132 representing connections between the nodes 131.

Referring to FIG. 1, at least some of the plurality of nodes 131 may be connected to generate the 2D graph 130 including the plurality of nodes 131 and the edges 132 representing connections between the nodes 131. An apparatus for generating a molecular structure may generate the 2D graph 130 of all possible combinations including a particular number of the nodes 131 and the edges 132 as described above. Each 2D graph 130 including the nodes 131 and the edges 132 may be transformed to correspond to the metal complex compound 100 including the metal atom 110 and the ligand 120 through a series of processes, described later.

Figure 2A:
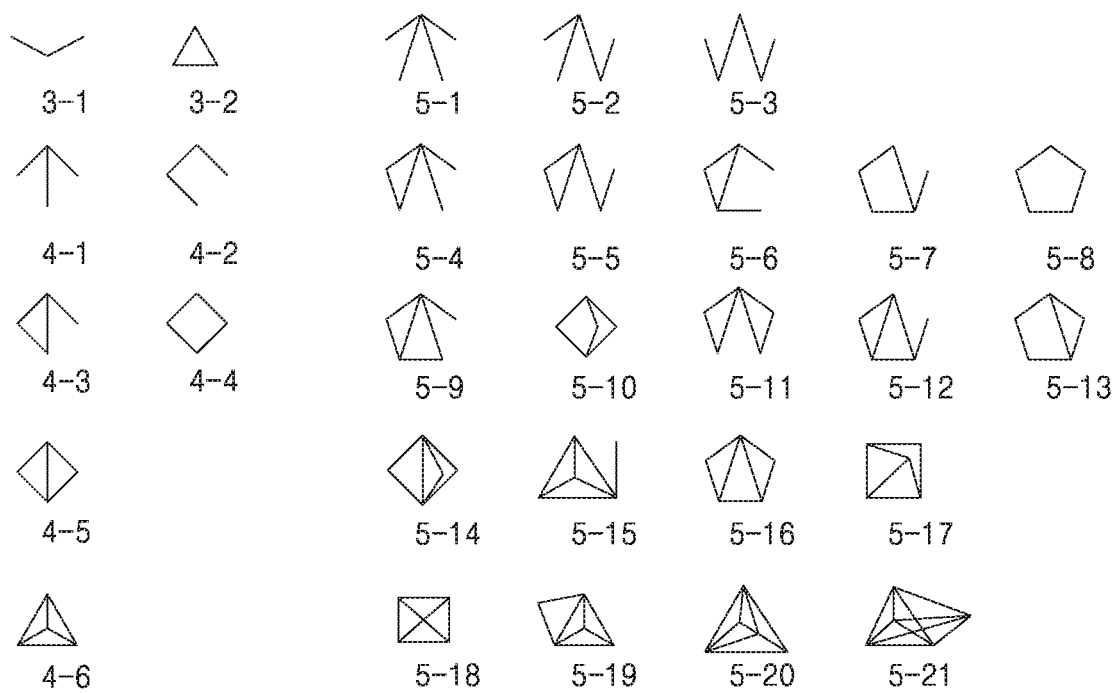
FIGS. 2A and 2B are diagrams illustrating 2D graphs of all possible combinations with respect to the number of nodes according to an embodiment.
Figure 2B:
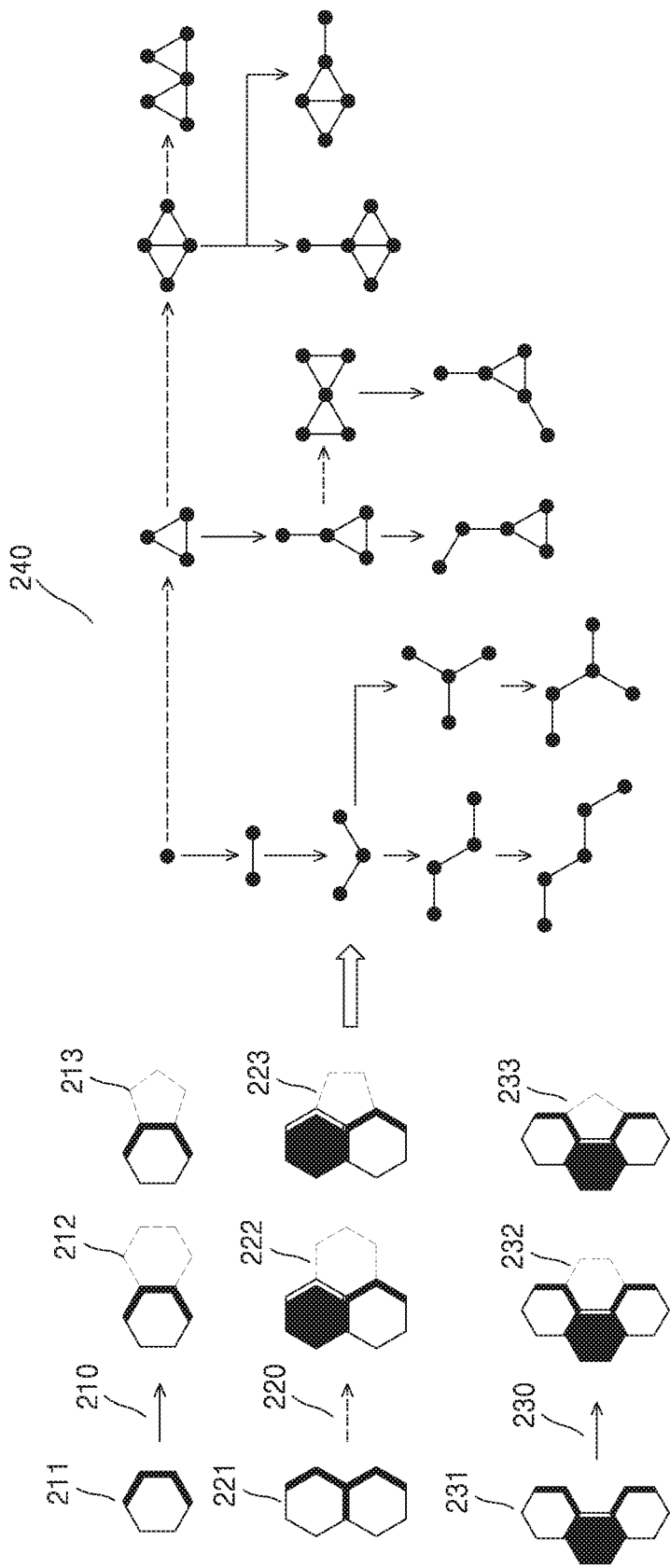

FIGS. 2A and 2B are diagrams illustrating 2D graphs of all possible combinations with respect to the number of nodes according to an embodiment.

Referring to FIG. 2A, the 2D graphs of all combinations that may include 3 to 5 nodes are shown. The 2D graphs may include fewer than three nodes or more than five nodes, but the 2D graphs that may include three to five nodes will be described for convenience of explanation.

An apparatus for generating a molecular structure may generate 2D graphs of all possible combinations including a particular number of nodes and edges representing connections between the nodes based on the number of the nodes constituting the 2D graph.

The molecular structure generating apparatus may generate the 2D graphs of all possible combinations including the plurality of nodes and edges representing connections by connecting at least some of the plurality of nodes. When a 2D graph includes three nodes, for example, the molecular structure generating apparatus may generate a 2D graph 3-1 in which the three nodes are connected in a line and a 2D graph 3-2 in which the three nodes are connected to each other. When a 2D graph includes four nodes, for example, the molecular structure generating apparatus may generate six 2D graphs 4-1 to 4-6. When a 2D graph includes five nodes, for example, the molecular structure generating apparatus may generate twenty-one 2D graphs 5-1 through 5-21. The above-noted examples in which 2D graphs having three nodes, four nodes, or five nodes are shown in FIG. 2A.

That is, the molecular structure generating apparatus may generate the 2D graphs of all combinations that may include three to five nodes, which means a total of twenty-nine 2D graphs.

Referring to FIG. 2B, 2D graphs that may be generated when each of nodes constituting a 2D graph is replaced with a polygonal ring structure having a pentagonal or hexagonal shape are shown.

In an embodiment, when the 2D graph includes three to five nodes having the pentagonal or hexagonal shape, the molecular structure generating apparatus may generate the 2D graphs of all combinations by using a first connection method 210 and a second connection method 220.

When a new hexagonal ring structure 212 or a new pentagonal ring structure 213 is bonded to an existing molecular structure, the molecular structure generating apparatus may apply the first connection method 210 such that the new ring structures 212 and 213 are bonded to only one ring structure 211 constituting the existing molecular structure. A process indicated by a solid line arrow in a structure diagram 240 represents the first connection method 210.

Also, when the new hexagonal ring structure 222 or the new pentagonal ring structure 223 is bonded to the existing molecular structure, the molecular structure generating apparatus may apply the second connection method 220 such that the new ring structure 222 and 223 are simultaneously bonded to two ring structures 221 constituting the existing molecular structure. A dashed line arrow in the structure diagram 240 represents the second connection method 220.

In an embodiment, when the 2D graph includes three to five nodes having the pentagonal or hexagonal shape, the molecular structure generating apparatus may generate a total of fourteen 2D graphs, as shown in structure diagram 240, by using the first connection method 210 and the second connection method 220. The 2D graphs in the structure diagram 240 that do not include three to five nodes are not counted among the fourteen 2D graphs.

In another embodiment, when the 2D graph includes six or more nodes, the molecular structure generating apparatus may further use a third connection method 230. When a new hexagonal ring structure 232 or a new pentagonal ring structure 233 is bonded to the existing molecular structure, the molecular structure generating apparatus may apply the third connection method 230 such that the new ring structure 232 and 233 are simultaneously bonded to three ring structures 231 constituting the existing molecular structure.

When a 2D graph is generated according to the above description in FIG. 2B, redundant 2D graphs may be generated. Therefore, the molecular structure generating apparatus may additionally perform a job of deleting some of the redundant 2D graphs.

Figure 3A:
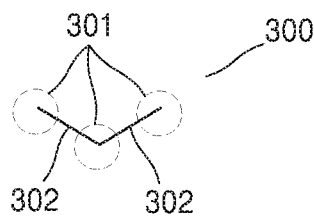
FIGS. 3A to 3C are diagrams for explaining an example of converting 2D graphs into molecular structures according to an embodiment.
Figure 3A:
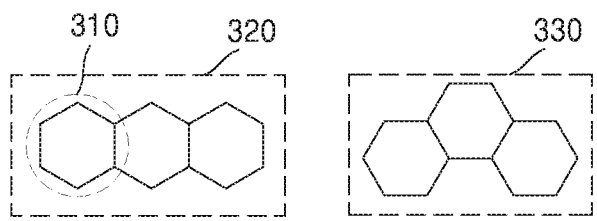
Figure 3A:
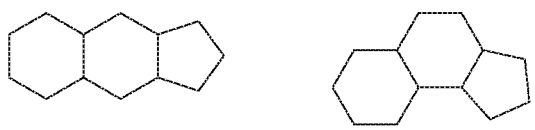
Figure 3A:
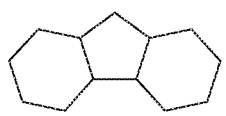
Figure 3A:
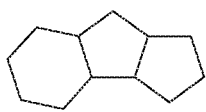
Figure 3A:
Figure 3A:
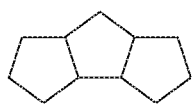
Figure 3B:
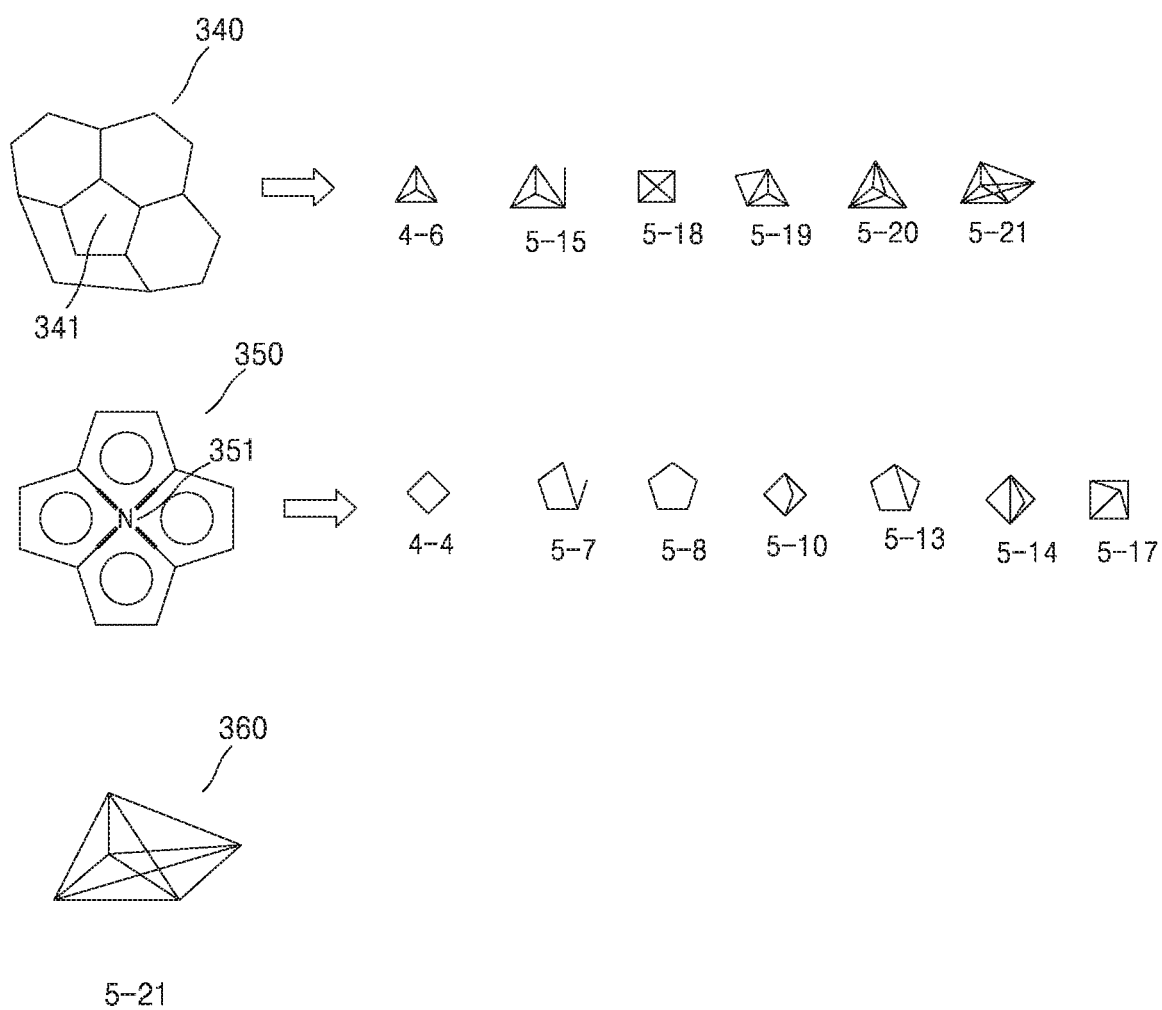
Figure 3C:
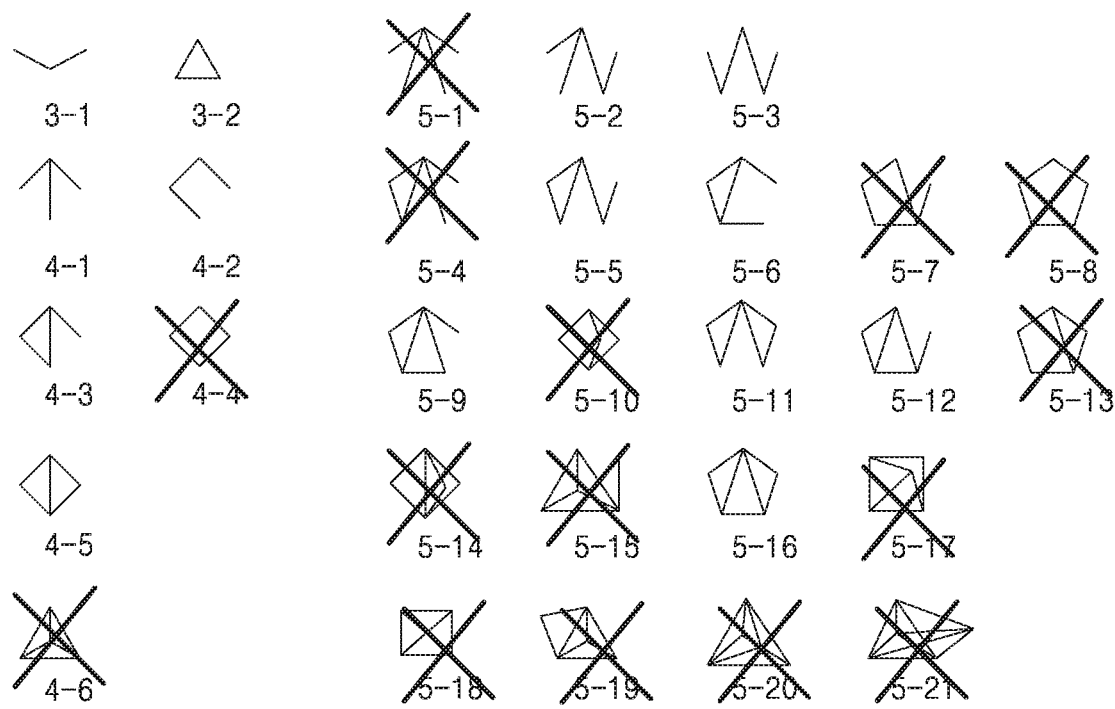

FIGS. 3A to 3C are diagrams for explaining an example of converting 2D graphs into molecular structures according to an embodiment.

A 2D graph including a plurality of nodes and edges representing connections between the nodes may be converted to a molecular structure. In an embodiment, the 2D graph may be converted into the molecular structure by replacing nodes included in the 2D graph with polygonal ring structures and replacing edges included in the 2D graph with a bond of the polygonal ring structures. The polygonal ring structure may include carbon atoms.

FIG. 3A shows an example of converting a 2D graph 300 in which three nodes 301 are connected to each other in a line into a molecular structure 320. An apparatus for generating a molecular structure may replace each of the nodes 301 of the 2D graph 300 with a polygonal ring structure 310 and replace each of edges 302 of the 2D graph 300 with a bond of the polygonal ring structures 310.

In an embodiment, the polygonal ring structure 310 may be either a pentagonal ring structure or a hexagonal ring structure. When each of the nodes 301 of the 2D graph 300 is replaced with any one of the pentagonal ring structure and the hexagonal ring structure, combinations of 'hexagonal-hexagonal-hexagonal', 'hexagonal-hexagonal-pentagonal', 'hexagonal-pentagonal-hexagonal', 'hexagonal-pentagonal-pentagonal', 'pentagonal-hexagonal-pentagonal', and 'pentagonal-pentagonal-pentagong' may be possible. Also, considering the bonding positions between the ring structures 310, two different molecular structures 320 and 330 may be generated for the ring structure combination of 'hexagonal-hexagonal-hexagonal'. As shown in FIG. 3A, two different molecular structures are also possible for the ring structure combinations of 'hexagonal-hexagonal-pentagonal' and 'pentagonal-hexagonal-pentagonal'. Considering the combination of the pentagonal ring structure and the hexagonal ring structure and the bonding positions between the ring structures 310, a total of nine molecular structures corresponding to the 2D graph 300 may be generated as shown in FIG. 3A.

In the same manner as above, the molecular structure generating apparatus may convert each of twenty-nine 2D graphs shown in FIG. 2 into the molecular structure including the polygonal ring structure (for example, the pentagonal ring structure and the hexagonal ring structure).

Referring to FIG. 3B, the molecular structure generating apparatus may analyze the converted molecular structures to remove a 2D graph corresponding to a molecular structure that does not meet a predetermined condition.

It is not possible for a pentagonal or hexagonal ring structure to be completely surrounded by fewer than five other ring structures. Accordingly, in an embodiment, the molecular structure generating apparatus may remove, among the converted molecular structures, a 2D graph corresponding to a molecular structure in which the number of peripheral ring structures surrounding a specific, completely surrounded ring structure is four or less.

For example, in the case of a molecular structure 340, since a central ring structure 341 is surrounded by four peripheral ring structures, the molecular structure generating apparatus may remove a 2D graph corresponding to the molecular structure 340. Referring to FIG. 2, when 2D graphs 4-6, 5-15, 5-18, 5-19, 5-20 and 5-21 are converted into molecular structures, the number of peripheral ring structures surrounding a specific ring structure may be four or less. That is, the molecular structure generating apparatus may remove the six 2D graphs 4-6, 5-15, 5-18, 5-19, 5-20 and 5-21 among a total of twenty-nine 2D graphs shown in FIG. 2.

It is also not possible for a single atom to be a part of four or more ring structures. Accordingly, the molecular structure generating apparatus may analyze the converted molecular structures to remove a 2D graph corresponding to a molecular structure in which four or more ring structures are bonded with respect to a specific atom. For example, in the case of a molecular structure 350, since four ring structures are bonded with respect to a central atom 351, the molecular structure generating apparatus may remove a 2D graph corresponding to the molecular structure 350. Referring to FIG. 2, when 2D graphs 4-4, 5-7, 5-8, 5-10, 5-13, 5-14 and 5-17 are converted into molecular structures, four or more ring structures may be bonded with respect to a specific atom. In other words, the molecular structure generating apparatus may remove the seven 2D graphs 4-4, 5-7, 5-8, 5-10, 5-13, 5-14 and 5-17 among the total of twenty-nine 2D graphs shown in FIG. 2.

Alternatively, the molecular structure generating apparatus may previously remove a 2D graph which may not be expressed within a plane without overlapping (i.e., crossing) edges among 2D graphs. For example, referring to FIG. 2, in the case of a 2D graph 360 corresponding to 5-21, since there are edges in the 2D graph that overlap each other, the molecular structure generating apparatus may remove the 2D graph 360 corresponding to 5-21.

A 2D graph may be converted into a molecular structure by replacing each of nodes constituting the 2D graph with either a pentagonal ring structure or a hexagonal ring structure. The number of possible molecular structures may increase rapidly according to the number of nodes constituting the 2D graph. Accordingly, rather than converting all 2D graphs into molecular structures, the computational complexity may be reduced by selecting a 2D graph corresponding to a predetermined molecular structure satisfying a predetermined condition and converting only the selected 2D graph into a molecular structure.

In an embodiment, the molecular structure generating apparatus may convert each of the total of 29 2D graphs shown in FIG. 2 into a molecular structure including a polygonal ring structure. Also, the molecular structure generating apparatus may remove, among the converted molecular structures, a 2D structure corresponding to a molecular structure in which the number of peripheral ring structures surrounding a specific ring structure is four or less when the specific ring structure is completely surrounded by the peripheral ring structures. Further, the molecular structure generating apparatus may remove a 2D graph corresponding to a molecular structure in which four or more ring structures are bonded with respect to a specific atom. 2D graphs corresponding to the molecular structure corresponding to the above-mentioned conditions among the total of 29 2D graphs shown in FIG. 2 are shown in FIG. 3.

Referring to FIG. 3C, fourteen 2D graphs may correspond to the above-described conditions among the total of 29 2D graphs. The molecular structure generating apparatus may convert each of the fourteen 2D graphs into a plurality of molecular structures by replacing nodes of the fourteen 2D graphs with any one of a pentagonal ring structure and a hexagonal ring structure and replacing edges with a bond between ring structures. The number of possible molecular structures of all possible combinations converted from the fourteen 2D graphs is shown in Table 1 below. That is, the number of molecular structures of all possible combinations converted from the fourteen 2D graphs is 405. According to the descriptions with reference to FIGS. 3A to 3C, when 2D graphs of all combinations that may include three to six nodes are converted into molecular structures, the number of molecular structures of all combinations that may be converted is 2594.

TABLE 1

| Ring structure | number of molecular structures |
|---|---|
| 3-1 | 9 |
| 3-2 | 4 |
| 4-1 | 4 |
| 4-2 | 31 |
| 4-3 | 14 |
| 4-5 | 9 |
| 5-2 | 22 |
| 5-3 | 141 |
| 5-5 | 62 |
| 5-6 | 42 |

TABLE 1-continued

| Ring structure | number of molecular structures |
|---|---|
| 5-9 | 12 |
| 5-11 | 7 |
| 5-12 | 28 |
| 5-16 | 20 |

Figure 4:
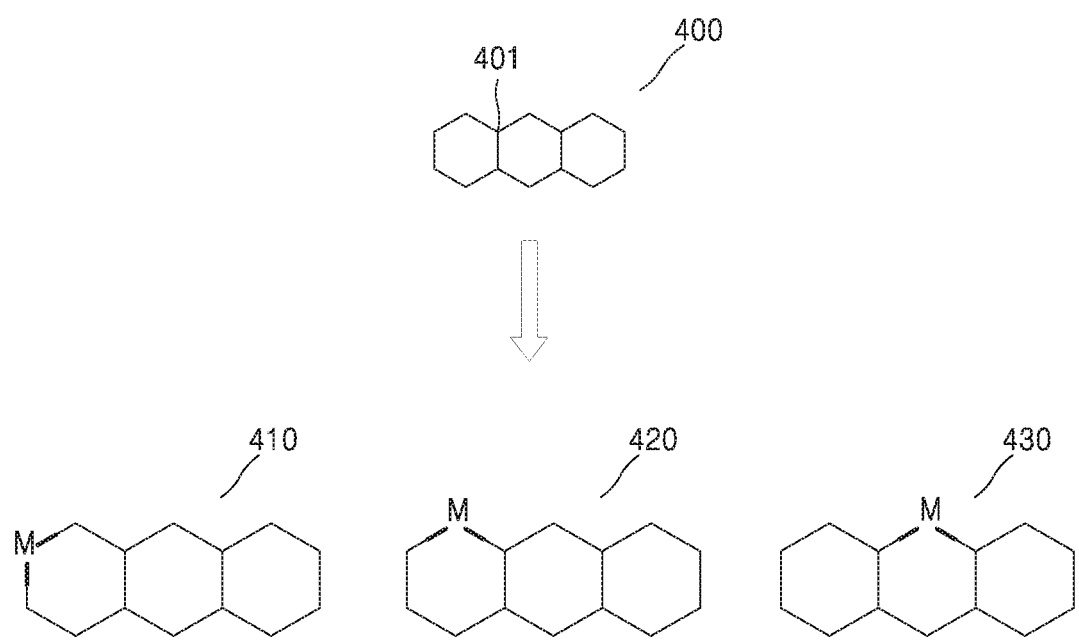
FIG. 4 is a diagram for explaining an example of substituting a metal atom for any one of carbon atoms included in a molecular structure according to an embodiment.

FIG. 4 is a diagram for explaining an example of substituting a metal atom for any one of carbon atoms included in a first molecular structure 400 according to an embodiment.

Referring to FIG. 4, an apparatus for generating a molecular structure may convert a 2D graph in which three nodes are connected to each other in a line into the first molecular structure 400 including three hexagonal ring structures. The hexagonal ring structures constituting the first molecular structure 400 may include carbon atoms at each vertex of the ring structures.

The molecular structure generating apparatus may substitute any one of the carbon atoms included in the first molecular structure 400 with an atom other than the carbon atoms. The molecular structure generating apparatus may substitute any one of the carbon atoms included in the first molecular structure 400 with a metal atom or a non-metal atom.

In an embodiment, the molecular structure generating apparatus may substitute any one of the carbon atoms included in the first molecular structure 400 with a metal atom based on a predetermined condition. For example, the molecular structure generating apparatus may substitute the metal atom for a carbon atom having a bond order of 2 from among the carbon atoms included in the first molecular structure 400. The carbon atom having the bond order of 2 means that a carbon atom is bonded with two other carbon atoms among the carbon atoms included in the first molecular structure 400. The carbon atom having the bond order of 2 may also be referred to as a secondary carbon atom.

Three second molecular structures 410 to 430 may be generated by substituting the carbon atom having a bond order of 2 of the first molecular structure 400 with the metal atom. In an embodiment, M representing the metal atom may be a platinum group element. The metal atom may include iridium (Ir), platinum (Pt), gold (Au), osmium (Os), etc., but is not limited thereto. Upon reviewing a position of the carbon atom substituted with the metal atom in the second molecular structures 410 to 430, it may be seen that the substituted carbon atoms are bonded to two other carbon atoms. That is, in the second molecular structures 410 to 430, the carbon atom having the bond order of 2 may be substituted with the metal atom. A carbon at a specific position 401 of the first molecular structure 400 may be a tertiary carbon atom having a bond order of 3 bonded to three other carbon atoms and may not be substituted with a metal atom under the condition that only the carbon atom having the bond order of 2 may be substituted with the metal atom.

In the case where only the carbon atom having the bond order of 2 among the carbons included in the first molecular structure 400 may be substituted with the metal atom, it is not possible to generate a molecular structure other than the second molecular structures 410 to 430 shown in FIG. 4. That is, the second molecular structures 410 to 430 may represent all possible combinations that may be generated by substituting the metal atom for the carbon atom having the bond order of 2 among the carbons included in the first molecular structure 400.

Figure 5A:
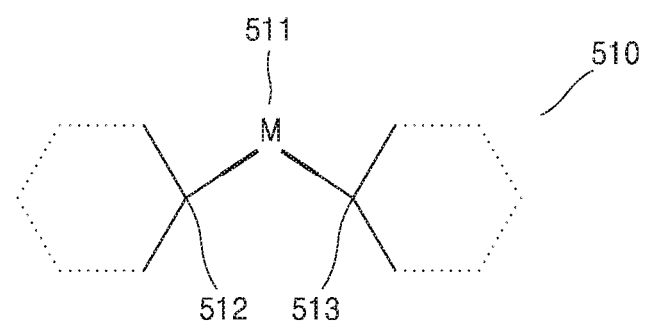
FIGS. 5A to 5C are diagrams for explaining an example of substituting a metal atom for any one of carbon atoms included in a molecular structure according to an embodiment.
Figure 5B:
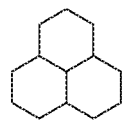
Figure 5B:
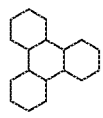
Figure 5B:
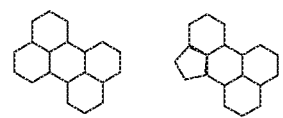
Figure 5C:
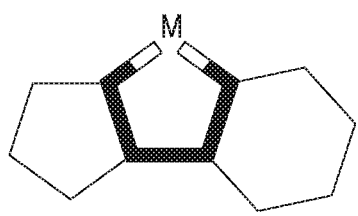
Figure 5C:
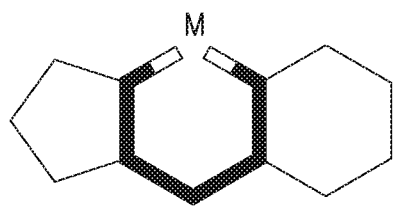

FIGS. 5A to 5C are diagrams for explaining an example of substituting a metal atom 511 for any one of carbon atoms included in a molecular structure 510 according to an embodiment.

A molecular structure generating apparatus may substitute any one of carbon atoms included in a molecular structure with a metal atom. The molecular structure generating apparatus may substitute any one of the carbon atoms included in the molecular structure with the metal atom based on a predetermined condition.

In an embodiment, the molecular structure generating apparatus may substitute any one of the carbon atoms included in the molecular structure with the metal atom and then select some of molecular structures based on a bond order of adjacent carbon atoms that are adjacent to the metal atom. For example, the molecular structure generating apparatus may select a molecular structure in which the bond order of the adjacent carbon atoms adjacent to the metal atom is 3 from molecular structures in which a carbon atom is substituted with the metal atom.

Referring to FIG. 5A, the molecular structure 510 in which a carbon atom having a bonding order of 2 is substituted with the metal atom 511 (for example, iridium (Ir), platinum (Pt), gold (Au) or osmium (Os)) is shown. At this time, a bond order of adjacent carbon atoms 512 and 513 adjacent to the metal atom 511 is 3.

Referring to FIG. 4, among the second molecular structures 410 to 430 shown in FIG. 4, a bond order of at least some of adjacent carbon atoms adjacent to a metal atom of the left and middle second molecular structures 410 and 420 may not be 3, whereas a bond order of all adjacent carbon atoms adjacent to a metal atom of the right second molecular structure 430 may be 3. That is, in the case of FIG. 4, under the condition that only those molecular structures are selected in which carbon atoms adjacent to the metal atom have a bond order of 3, the molecular structure generating apparatus may finally select only the right second molecular structure 430.

Referring to FIG. 5B, in the case of three 2D graphs 3-2, 4-1 and 5-11 among fourteen 2D graphs shown in FIG. 3C, even when a carbon atom of any position among carbon atoms included in the molecular structure is substituted with a metal atom, a bond order of at least some of adjacent carbon atoms adjacent to the metal atom may not be 3. That is, the molecular structure generating apparatus may select only the remaining eleven 2D graphs, excluding the three 2D graphs 3-2, 4-1 and 5-11, from among fourteen 2D graphs shown in FIG. 3C.

The molecular structure generating apparatus may convert a 2D graph including a plurality of nodes and edges representing connections between the nodes into a first molecular structure. At this time, by analyzing the first molecular structure, the molecular structure generating apparatus may remove a 2D graph corresponding to the first molecular structure which does not meet a predetermined condition, examples of which are set forth above. Further, the molecular structure generating apparatus may substitute any one of carbon atoms included in the first molecular structure with a metal atom based on a predetermined condition, examples of which are set forth above.

Based on the descriptions provided with reference to FIGS. 2 to 4 and 5A and 5B, the molecular structure generating apparatus may select only the eleven 2D graphs 3-1, 4-2, 4-3, 4-5, 5-2, 5-3, 5-5, 5-6, 5-9, 5-11, 5-12 and 5-16 from twenty-nine 2D graphs shown in FIG. 2 and convert the selected eleven 2D graphs and generate a second molecular structure. Any one of carbon atoms included in the second molecular structure may be substituted with a metal atom.

In this case, referring to FIG. 5C, a total of 594 second molecular structures may be generated. Among them, there are 262 second molecular structures have the metal atom included in a pentagonal ring structure, and there are 332 second molecular structures have the metal atom included in a hexagonal ring structure.

Figure 6:
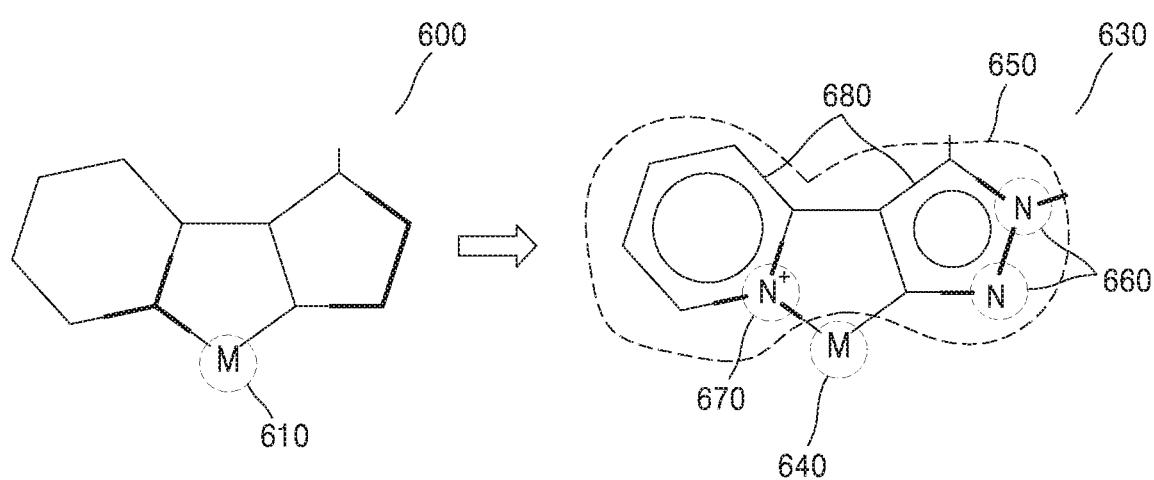
FIG. 6 is a diagram for explaining an example of a finally generated metal complex compound according to an embodiment.

FIG. 6 is a diagram for explaining an example of a finally generated metal complex compound 630 according to an embodiment.

Referring to FIG. 6, one of carbon atoms included in a molecular structure 600 may be substituted with a metal atom 610. In an embodiment, the carbon atom included in the molecular structure 600 may be substituted with the metal atom 610 based on the description provided with reference to FIGS. 4 and 5A to 5C.

Further, a molecular structure generating apparatus may substitute at least one of the carbon atoms included in the molecular structure 600 with a non-metal atom other than a carbon atom. For example, the molecular structure generating apparatus may substitute at least one of the carbon atoms included in the molecular structure 600 with any one of nitrogen (N), oxygen (O), phosphorus (P), sulfur (S), selenium (Se), and silicon (Si).

In an embodiment, the molecular structure generating apparatus may substitute at least one of the carbon atoms included in the molecular structure 600 with a nitrogen atom 660. To reduce the complexity of calculation, the total number of carbon atoms substituted with nitrogen atoms in the molecular structure 600 may be 5 or less. Also, the number of carbon atoms substituted with the nitrogen atoms per ring structure constituting the molecular structure 600 may be 3 or less.

In an embodiment, the molecular structure generating apparatus may substitute at least one of the carbon atoms included in the molecular structure 600 with an oxygen atom. The total number of carbon atoms substituted with oxygen atoms in the molecular structure 600 may be 1 or less.

In an embodiment, the molecular structure generating apparatus may substitute at least one of the carbon atoms included in the molecular structure 600 with a +1 nitrogen ion $N^+$ 670. The molecular structure generating apparatus may substitute carbon atoms adjacent to the metal atom 640 with the +1 nitrogen ion $N^+$ 670.

In an embodiment, one or more of adjacent ring structures 680 adjacent to a ring structure including the metal atom 640 may be aromatic rings.

The molecular structure generating apparatus may finally generate the metal complex compound 630 including the metal atom 640 and a ligand 650. The metal complex compound 630 may include at least one nitrogen atom 660, an oxygen atom and the +1 nitrogen ion $N^+$ 670. At least some of ring structures constituting the metal complex compound 630 may be aromatic rings.

Referring to FIG. 5C, when some of the carbon atoms included in the 594 second molecular structures are substituted with nitrogen atoms and the number of the substituted nitrogen atoms is set to 5 or less, the molecular structure generating apparatus may generate about 10 million final molecular structures (for example, metal complex compounds) from the 594 second molecular structures. That is, final molecular structures of all possible combinations from the 594 second molecular structures may be about 10 million. The final molecular structures may be stored in a memory of the molecular structure generating apparatus or transferred to an external server. The molecular structure generating apparatus may perform duplicate inspection to see whether there is any redundancy between the final molecular structures.

The molecular structure generating apparatus may systematically generate molecular structures of all possible combinations through the method described above with reference to FIGS. 1 to 6. That is, the molecular structure generating apparatus may generate molecular structures of all possible combinations (for example, metal complex compounds) satisfying a predetermined condition from 2D graphs of all possible combinations including a plurality of nodes and edges representing connections between the nodes.

Figure 7:
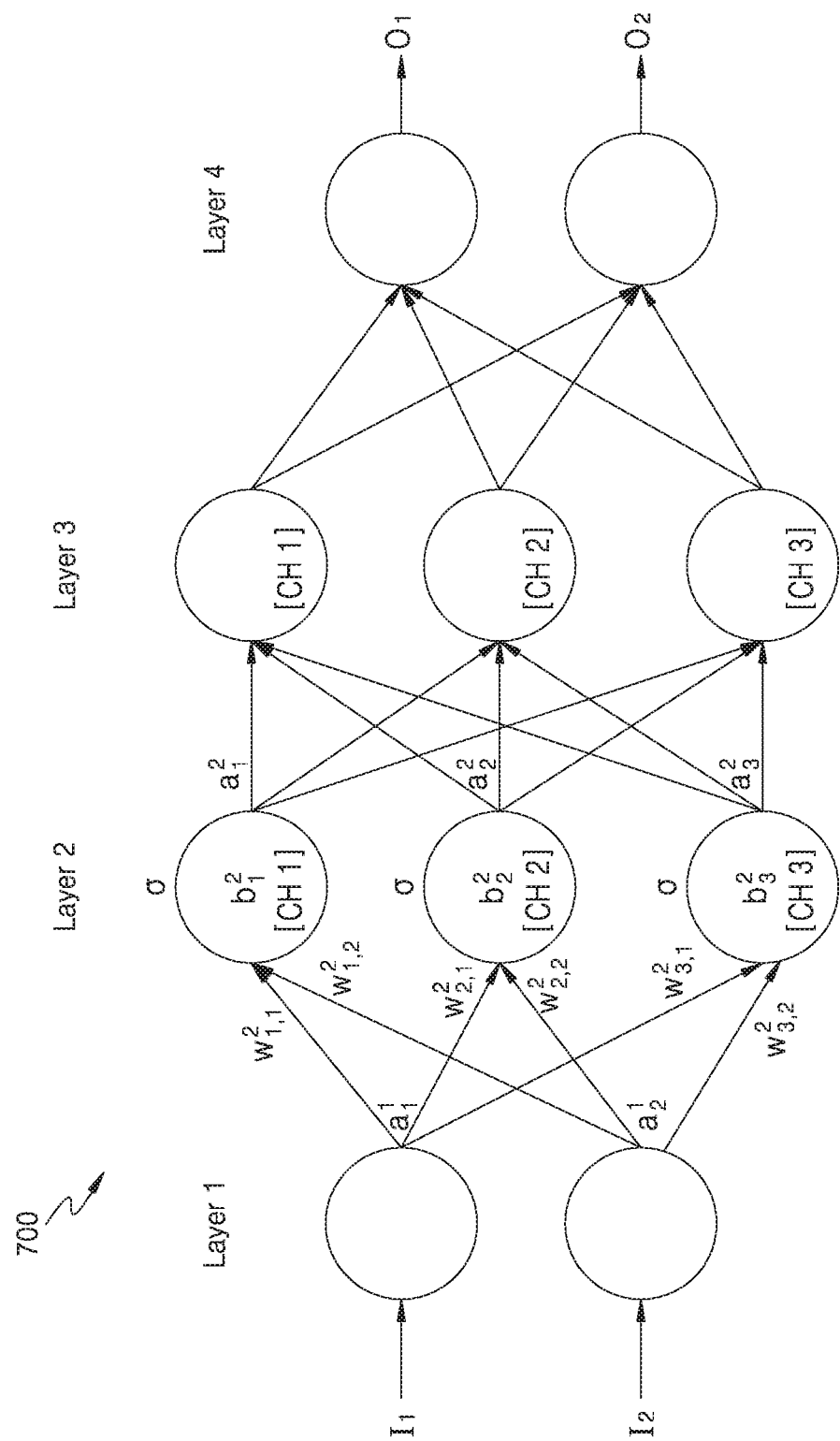
FIG. 7 is a diagram for describing a computation performed by a deep neural network (DNN) according to an embodiment.

FIG. 7 is a diagram for describing a computation performed by a deep neural network (DNN) 700 according to an embodiment.

Referring to FIG. 7, a DNN 700 has a structure including an input layer, hidden layers, and an output layer, performs a computation based on received input data (e.g., $I_1$ and $I_2$), and generates output data (e.g., $O_1$ and $O_2$) based on a computation result.

For example, as illustrated in FIG. 7, the DNN 700 may include an input layer (Layer 1), two hidden layers (Layer 2 and Layer 3), and an output layer (Layer 4). Since the DNN 700 may include many layers to process valid information, the DNN 700 may process complex data compared to a neural network including a single layer. Although the DNN 700 illustrated in FIG. 2 includes 4 layers, the DNN 700 is only an example and may also include more or fewer layers and more or fewer channels than those illustrated therein. That is, the DNN 700 may have various structures of layers different from that illustrated in FIG. 7.

Each of the layers included in the DNN 700 may have a plurality of channels. The channels may correspond to a plurality of artificial nodes known as neurons, processing elements (PEs), units, or similar terms. For example, as illustrated in FIG. 7, Layer 1 may include two channels (nodes), and Layers 2 and 3 may include three channels respectively. However, the layers are only examples and each of the layers included in the DNN 700 may have various numbers of channels (nodes).

The channels included in each of the layers of the DNN 700 may be interconnected to process data. For example, a channel may perform a computation of data received from channels of one layer and output a computation result to channels of another layer. In FIG. 7, for example, the channels included in Layer 2 receive data from the channels included in Layer 1 and output a computation result to the channels included in Layer 3.

Input and output of each channel may be referred to as input activation and output activation. That is, an activation may be not only an output of one channel but also a parameter corresponding to an input of channels included in a successive layer. Each of the channels may determine an activation thereof based on activations and weights received from channels included in a previous layer. The weight is a parameter used to calculate the output activation of each channel and may be a value assigned to the relationship between channels.

Each of the channels may be processed by a computational unit or a processing element that receives an input and outputs an output activation. The input-output of each channel may be mapped. For example, when σ is an activation function, $w_{jk}^i$ is a weight from a $k^{th}$ channel included in an layer to a $j^{th}$ channel included in an $i^{th}$ layer, $b_j^i$ is a bias of the $j^{th}$ channel included in the $i^{th}$ layer, and $a_j^i$ is an activation of the $j^{th}$ channel of the $i^{th}$ layer, an activation $a_j^i$ may be calculated using Equation 1 below.

$$a_j^i = \sigma\left(\sum_k (w_{jk}^j \times a_k^{i-1}) + b_j^i\right) \quad \text{[Equation 1]}$$

As illustrated in FIG. 7, an activation of a first channel CH1 of a second layer Layer 2 may be expressed as $a_1^2$. In addition, $a_1^2$ may have a value of $a_1^2 = \sigma(w_{1,1}^2 \times a_1^1 + w_{1,2}^2 \times a_2^1 + b_1^2)$ according to Equation 1. However, the above-described Equation 1 is only an example for describing the activation and the weight used to process data in the DNN 700 and the embodiment is not limited thereto. The activation may be a value obtained by inputting a sum of activations received from the previous layer to an activation function and processing the result with a rectified linear unit (ReLU).

An apparatus for generating a molecular structure may arbitrarily select some of the about 10 million final molecular structures generated through series of processes described above with reference to FIGS. 1 to 6. The molecular structure generating apparatus may calculate a specific property value by applying a DFT (Density Function Theory) simulation to the selected final molecular structures. For example, the molecular structure generating apparatus may arbitrarily select about 50,000 final molecular structures from the about 10 million final molecular structures to apply the DFT simulation and calculate a physical property value with respect to each of the about 50,000 final molecular structures. The specific property value may include, but is not limited to, a refractive index value, an elastic modulus, a melting point, a transmission wavelength, an emission wavelength, etc.

The molecular structure generating apparatus may train the DNN 700 by using the arbitrarily selected final molecular structures and data obtained by matching the specific property value with respect to each of the final molecular structures. Specifically, the molecular structure generating apparatus may use a descriptor as input data of the DNN 700. For example, the molecular structure generating apparatus may use ECFP (Extended Connectivity Fingerprint) as the input data of the DNN 700 as the descriptor of the selected final molecular structures.

When the descriptor of the final molecular structures is input to the DNN 700, the property value may be calculated from output data. For example, the property value output from the DNN 700 may be the $T_1$ energy level value indicating the characteristics of an OLED dopant.

The DNN 700 may determine a factor defining the relationship between a descriptor and a property via learning using descriptors and property values. That is, among Layers 1 to 4 constituting the DNN 700, the descriptor corresponds to the input layer (Layer 1), the property value corresponds to the output layer (Layer 4), and the factor corresponds to at least one hidden layer (Layer 2 and/or Layer 3).

The molecular structure generating apparatus may finally obtain the specific predicted property values with respect to all of the about 10 million final molecular structures generated through the series of processes described above with reference to FIGS. 1 to 6 by using the descriptor of the remaining final molecular structures as the input data in the completely trained DNN 700. For example, the molecular structure generating apparatus may obtain the predicted $T_1$ energy level value with respect to all of the about 10 million final molecular structures using the completely trained DNN 700.

Figure 8:
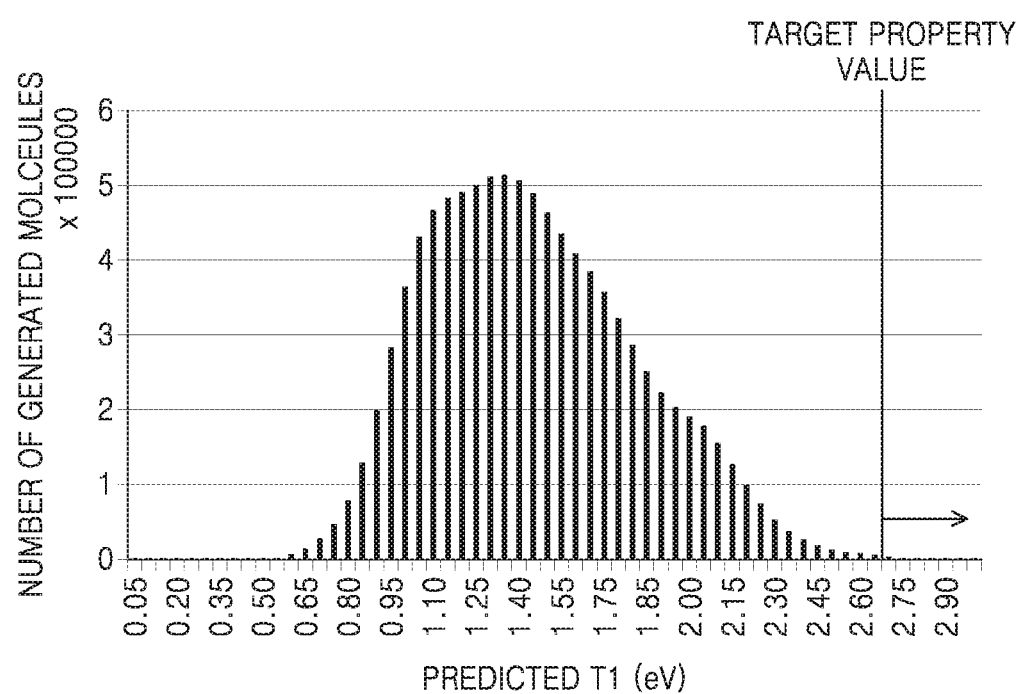
FIG. 8 is a graph showing a $T_1$ energy level value with respect to each of final molecular structures according to an embodiment.

FIG. 8 is a graph showing a predicted $T_1$ energy level value with respect to each of final molecular structures according to an embodiment.

Referring to FIG. 8, the predicted $T_1$ energy level value with respect to each of about 10 million final molecular structures obtained using the DNN 700 of FIG. 7 is shown. An apparatus for generating a molecular structure may set a target property value to obtain a final molecular structure that satisfies the set target property value.

For example, when the target physical property value with respect to the $T_1$ energy level value is 2.70 eV, the apparatus for generating a molecular structure may selectively obtain only those final molecular structures having the predicted $T_1$ energy level value of 2.70 eV or more. Referring to FIG. 8, among about 10 million final molecular structures, since the predicted $T_1$ energy level value of about 25,000 final molecular structures corresponding to 1.04% is 2.70 eV, the molecular structure generating apparatus may selectively obtain only the about 25,000 final molecular structures.

The molecular structure generating apparatus may generate molecular structures of all possible combinations satisfying a predetermined condition from 2D graphs of all possible combinations including a plurality of nodes and edges representing connections between the nodes. That is, the molecular structure generating apparatus may systematically generate molecular structures of all possible combinations and obtain specific physical property values with respect to all the generated molecular structures by using DFT simulation and DNN. Also, the molecular structure generating apparatus may selectively obtain only molecular structures having the target property value by comparing the predetermined target property value with a predicted specific property value of each of the molecular structures.

Figure 9:
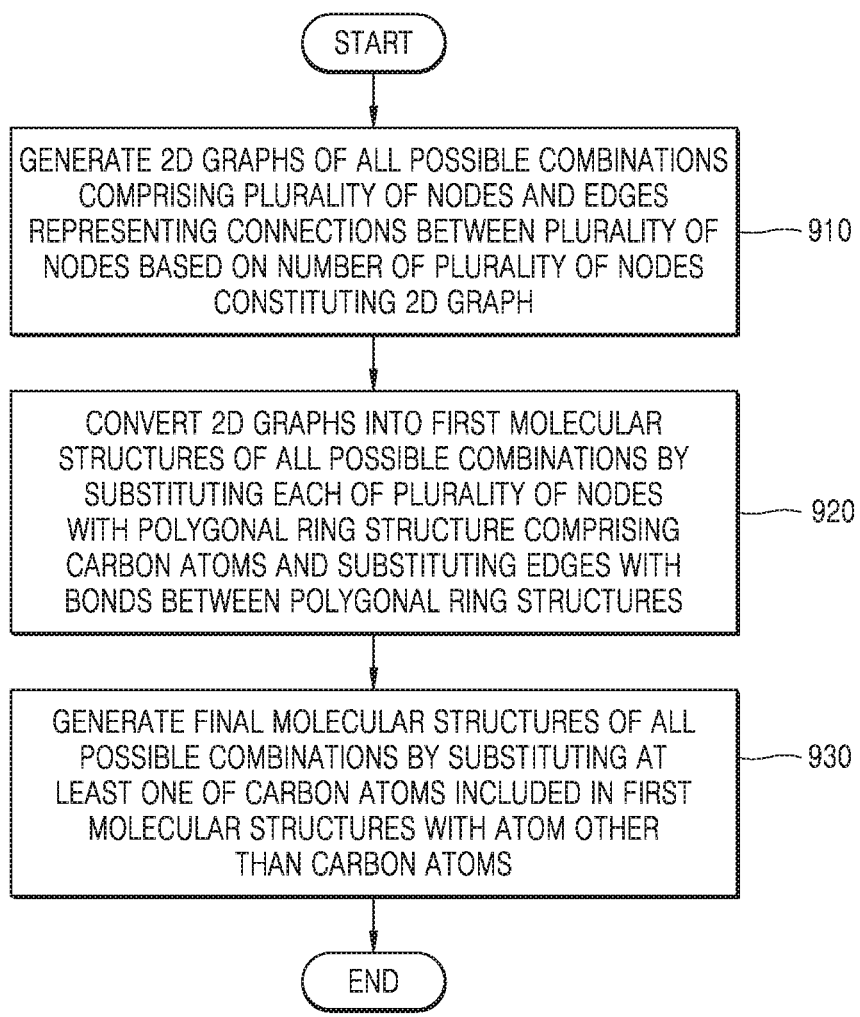
FIG. 9 is a flowchart illustrating a method of generating a molecular structure according to an embodiment.

FIG. 9 is a flowchart illustrating a method of generating a molecular structure according to an embodiment.

Referring to FIG. 9, in operation 910, a molecular structure generating apparatus may generate 2D graphs of all possible combinations including a plurality of nodes and edges representing connections between the nodes, based on the number of the nodes constituting the 2D graphs.

In an embodiment, any molecular structure may be represented as a 2D graph including nodes and edges. At this time, the nodes of the 2D graph may represent each of ring structures constituting the molecular structure, and the edges between the nodes may represent atomic bonds between the ring structures.

The molecular structure generating apparatus may remove a 2D graph that does not meet a predetermined condition among the generated 2D graphs. For example, the molecular structure generating apparatus may remove a 2D graph that may not be expressed in a plane without overlapping edges in the 2D graph.

In operation 920, the molecular structure generating apparatus may convert the 2D graphs into first molecular structures of all possible combinations by substituting each of the plurality of nodes with a polygonal ring structure including carbon atoms and substituting the edges with bonds between polygonal ring structures.

According to shapes of ring structures (e.g., pentagonal ring structures and hexagonal ring structures) and bond positions between the ring structures, a single 2D graph may be converted into a plurality of first molecular structures.

By analyzing the converted molecular structure, the molecular structure generating apparatus may remove a 2D graph corresponding to a molecular structure that does not meet a predetermined condition. In an embodiment, the molecular structure generating apparatus may remove a 2D graph corresponding to a molecular structure in which the number of peripheral ring structures surrounding a completely surrounded specific ring structure is four or less. Also, the molecular structure generating apparatus may analyze the converted molecular structure to remove a 2D graph corresponding to a molecular structure in which four or more ring structures are coupled around a specific atom.

In operation 930, the molecular structure generating apparatus may generate final molecular structures of all possible combinations by substituting at least one of the carbon atoms included in the first molecular structure with an atom other than a carbon atom.

In an embodiment, the molecular structure generating apparatus may substitute a carbon atom included in the first molecular structure with a metal atom. For example, the molecular structure generating apparatus may substitute the carbon atom with any one of iridium (Ir), platinum (Pt), gold (Au), and osmium (Os).

Further, the molecular structure generating apparatus may substitute the carbon atoms included in the first molecular structure with non-metal atoms. For example, the molecular structure generating apparatus may substitute the carbon atoms with any one of nitrogen (N), oxygen (O), phosphorus (P), sulfur (S), selenium (Se) and silicon (Si). However, kinds of substituted atoms are not limited thereto.

That is, the final molecular structure generated by the molecular structure generating apparatus may be a metal complex compound including metal atoms or may be an organic molecule including no metal atom.

In an embodiment, the molecular structure generating apparatus may generate a second molecular structure by substituting a carbon atom having a bond order of 2 (i.e., a carbon atom that is bonded to two other atoms) into a metal atom. The molecular structure generating apparatus may also generate the second molecular structure by substituting a carbon atom itself having a bond order of 2, with each of the two adjacent carbon atom having a bond order of 3 (i.e., a carbon atom that is bonded to three other atoms).

Also, the molecular structure generating apparatus may generate the final molecular structures of all possible combinations by substituting at least one of the carbon atoms included in the second molecular structure with a nitrogen atom or an oxygen atom.

The molecular structure generating apparatus may substitute at least one of the carbon atoms included in the second molecular structure with the nitrogen atom or the oxygen atom based on a predetermined condition.

In an embodiment, the total number of carbon atoms substituted with nitrogen atoms in the molecular structure may be 5 or less. The number of carbon atoms substituted with the nitrogen atoms per ring structure constituting the molecular structure may be 3 or less. Also, the total number of carbon atoms substituted with oxygen atoms in the molecular structure may be one or less.

In an embodiment, the molecular structure generating apparatus substitute at least one of the carbon atoms included in the molecular structure with a +1 nitrogen ion $N^+$. The molecular structure generating apparatus may substitute carbon atoms adjacent to the metal atom with the +1 nitrogen ion $N^+$.

In an embodiment, one or more adjacent ring structures adjacent to a ring structure including the metal atom may be aromatic rings.

The molecular structure generating apparatus may calculate specific property values of the final molecular structures of all possible combinations generated through operations 910 to 930. In an embodiment, the molecular structure generating apparatus may arbitrarily select some of the final molecular structures, apply a DFT (Density Function Theory) simulation to the selected final molecular structures and obtain the specific property values. The molecular structure generating apparatus may train a DNN by using the arbitrarily selected final molecular structures and data matching the specific property value with respect to each of the final molecular structures. The molecular structure generating apparatus may use the completely trained DNN to calculate specific property values with respect to the remaining final molecular structures. Through the above-described process, the molecular structure generating apparatus may systematically generate molecular structures of all possible combinations.

Figure 10:
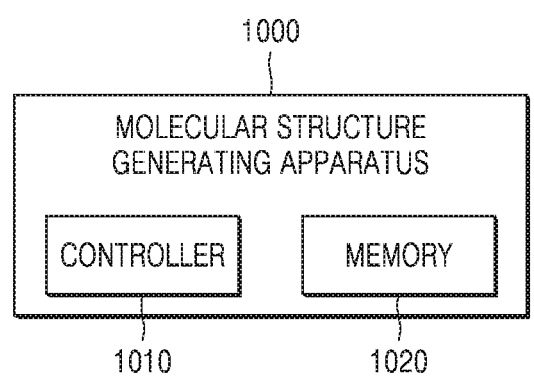
FIG. 10 is a block diagram showing a hardware configuration of a molecular structure generating apparatus according to an embodiment.

FIG. 10 is a block diagram showing a hardware configuration of a molecular structure generating apparatus 1000 according to an embodiment.

Referring to FIG. 10, the molecular structure generating apparatus 1000 may include a controller 1010 and a memory 1020. FIG. 10 only illustrates components of the molecular structure generating apparatus 1000 related to the embodiments of the present disclosure. Thus, it is obvious to those skilled in the art that the molecular structure generating apparatus 1000 may further include any other general-purpose components in addition to the components shown in FIG. 10.

The molecular structure generating apparatus 1000 may be implemented as various types of devices such as a personal computer (PC), a server device, a mobile device, an embedded device, etc.

The controller 1010 may control a series of processes for generating the molecular structure described above with reference to FIGS. 1 to 9. The controller 1010 controls the overall function for controlling the molecular structure generating apparatus 1000. For example, the controller 1010 controls the overall operation of the molecular structure generating apparatus 1000 by executing programs stored in the memory 1020 of the molecular structure generating apparatus 1000. The controller 1010 may be implemented as a central processing unit (CPU), a graphics processing unit (GPU), an application processor (AP), and the like provided in the molecular structure generating apparatus 1000 but is not limited thereto.

The memory 1020 is a hardware component that stores a variety of data processed in the molecular structure generating apparatus 1000 and may store applications, drivers, etc. to be processed by the molecular structure generating apparatus 1000. The memory 1020 may include random access memory (RAM) such as dynamic random access memory (DRAM) and static random access memory (SRAM), read-only memory (ROM), electrically erasable programmable read-only memory (EEPROM), CD-ROM, Blue-ray, or other optical disk storage, hard disk drive (HDD), solid state drive (SSD), or a flash memory.

The molecular structure generating apparatus 1000 may further include a communicator (not shown). The molecular structure generating apparatus 1000 may receive data from an external server through a communicator (not shown) or to transmit data to an external server. The communicator (not shown) may include a local communicator, a mobile communicator, and a broadcast receiver. The molecular structure generating apparatus 1000 may further include a user interface (not shown). The user interface refers to a device used to input data to control the molecular structure generating apparatus 1000. Examples of the user interface may include, but are not limited to, a key pad, a dome switch, a touch pad (e.g., capacitive overlay type, resistive overlay type, infrared beam type, surface acoustic wave type, integral strain gauge type, and piezo electric type), a jog wheel, a jog switch, etc.

The molecular structure generating apparatus 1000 may include a neural network apparatus. The neural network apparatus may be implemented as various types of devices such as a personal computer (PC), a server device, a mobile device, an embedded device, etc. Examples of the neural network apparatus may include, but are not limited to, a smartphone, a tablet device, an augmented reality (AR) device, an Internet of Things (IoT) device, an autonomous vehicle, a robot, a medical device, and the like which perform speech recognition, image recognition, image classification, and the like using a neural network. Furthermore, the neural network apparatus may be a dedicated hardware (HW) accelerator mounted on the devices described above. The neural network apparatus may be a hardware accelerator such as a neural processing unit (NPU), a tensor processing unit (TPU), and a neural engine, which are dedicated modules for driving a neural network but is not limited thereto.

The aforementioned embodiments may be embodied in the form of a recording medium including instructions executable by a computer, such as a program module, executed by a computer. The computer-readable medium may be any recording medium that may be accessed by a computer and may include volatile and non-volatile media and removable and non-removable media. Also, the computer-readable medium may include computer storage media and communication media. The computer storage media include volatile and non-volatile and removable and non-removable media implemented using any method or technology to store information such as computer-readable instructions, data structures, program modules, or other data. The communication media include computer-readable instructions, data structures, program modules, or other data in a modulated data signal, or other transport mechanisms and include any delivery media.

Also, throughout the specification, the term "unit" may be a hardware component such as a processor or a circuit and/or a software component executed by the hardware component such as a processor.

The above description of the present disclosure is provided for the purpose of illustration, and it would be understood by those skilled in the art that various changes and modifications may be made without changing technical conception and essential features of the present disclosure. Thus, it is clear that the above-described illustrative embodiments are illustrative in all aspects and do not limit the present disclosure. For example, each component described to be of a single type may be implemented in a distributed manner. Likewise, components described to be distributed may be implemented in a combined manner.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. A method of generating a molecular structure, the method comprising:
    generating, based on a predetermined number of a plurality of nodes, all possible two-dimensional (2D) graphs including the predetermined number of nodes and a plurality of edges representing connections between the plurality of nodes;
    for each 2D graph from among the generated 2D graphs, generating all possible molecular structures based on the 2D graph that meet a predetermined condition by:
        substituting each of the plurality of nodes with a polygonal ring structure including carbon atoms,
        substituting the plurality of edges with bonds between polygonal ring structures; and
        substituting at least one of the carbon atoms included in the polygonal ring structures with an atom other than a carbon atom,
    selecting some of the generated molecular structures;
    calculating a specific property value with respect to each of the selected molecular structures; and
    training a neural network by using a descriptor of the selected molecular structures as input data of the neural network and using the specific property value corresponding to each of the selected molecular structures as output data of the neural network,
    wherein the predetermined condition comprises:
        in the molecular structures corresponding to the 2D graphs, a number of peripheral ring structures surrounding a specific ring structure,
        in the molecular structures corresponding to the 2D graphs, a number of ring structures bonded around a specific atom, and
        in the 2D graphs, whether edges of a 2D graph are expressed within a plane without overlapping.

2. The method of claim 1, wherein the substituting the at least one of the carbon atoms comprises:
    substituting a first carbon atom from among the carbon atoms included in the polygonal ring structures with a metal atom; and
    substituting at least one second carbon atom from among the carbon atoms included in the polygonal ring structures with any one of nitrogen (N), oxygen (O), phosphorus (P), sulfur (S), selenium (Se), and silicon (Si).

3. The method of claim 2, wherein the first carbon atom is a carbon atom having a bond order of 2 from among the carbon atoms included in the polygonal ring structures.

4. The method of claim 3, wherein a bond order of adjacent carbon atoms adjacent to the metal atom is 3.

5. The method of claim 1, wherein each of the polygonal ring structures is any one from among a pentagonal ring structure and a hexagonal ring structure.

6. The method of claim 1, wherein each of the generated 2D graphs comprises three to five nodes.

7. The method of claim 1, wherein an adjacent polygonal ring structure adjacent to a polygonal ring structure including the metal atom is an aromatic ring.

8. The method of claim 1, further comprising:
    calculating the specific property value with respect to an arbitrary molecular structure from among the generated molecular structures by using at least some of the generated molecular structures and the neural network, the neural network being trained based on matching data obtained by matching each of the at least some of the generated molecular structures with a corresponding property value.

9. A non-transitory computer readable recording medium comprising a program, which when executed by a computer, performs the method of claim 1.

10. An apparatus for generating a molecular structure, the apparatus comprising:
a memory storing at least one program; and
a processor configured to drive the apparatus for generating the molecular structure by executing the at least one program,
wherein the processor is further configured to:
generate, based on a predetermined number of a plurality of nodes, all possible two-dimensional (2D) graphs including the predetermined number of nodes and a plurality of edges representing connections between the plurality of nodes,
for each 2D graph from among the generated 2D graphs, generating all possible molecular structures based on the 2D graph that meet a predetermined condition by:
substituting each of the plurality of nodes with a polygonal ring structure comprising carbon atoms,
substituting the plurality of edges with bonds between polygonal ring structures, and
substituting at least one of the carbon atoms included in the polygonal ring structures with an atom other than a carbon atom,
select some of the generated molecular structures;
calculate a specific property value with respect to each of the selected molecular structures; and
train a neural network by using a descriptor of the selected molecular structures as input data of the neural network and using the specific property value corresponding to each of the selected molecular structures as output data of the neural network,
wherein the predetermined condition comprises:
in the molecular structures corresponding to the 2D graphs, a number of peripheral ring structures surrounding a specific ring structure,
in the molecular structures corresponding to the 2D graphs, a number of ring structures bonded around a specific atom, and
in the 2D graphs, whether edges of a 2D graph are expressed within a plane without overlapping.

11. The apparatus of claim 10, wherein the processor is further configured to substitute a first carbon atom from among the carbon atoms included in the first molecular structures with a metal atom and substitute at least one second carbon atom from among the carbon atoms included in the polygonal ring structures with any one of nitrogen (N), oxygen (O), phosphorus (P), sulfur (S), selenium (Se), and silicon (Si).

12. The apparatus of claim 11, wherein the first carbon atom is a carbon atom having a bond order of 2 from among the carbon atoms included in the polygonal ring structures.

13. The method of claim 12, wherein a bond order of adjacent carbon atoms adjacent to the metal atom is 3.

14. The apparatus of claim 11, wherein an adjacent polygonal ring structure adjacent to a polygonal ring structure comprising the metal atom is an aromatic ring.

15. The apparatus of claim 10, wherein each of the polygonal ring structures is any one from among a pentagonal ring structure and a hexagonal ring structure.

16. The apparatus of claim 10, wherein each of the generated 2D graphs comprises three to five nodes.

17. The apparatus of claim 9, wherein the processor is further configured to calculate the specific property value with respect to an arbitrary molecular structure from among the generated molecular structures by using at least some of the generated molecular structures and a neural network, the neural network being trained based on matching data obtained by matching each of the at least some of the generated molecular structures with a corresponding property value.

* * * * *